United States Patent [19]

Black et al.

[11] Patent Number: 5,037,813
[45] Date of Patent: Aug. 6, 1991

[54] N-ALKYL-N-[1,3-BUTADIENYL(THIO)CARBONYL]-(THIO) PHOSPHORAMIDATES, COMPOSITIONS, AND METHODS OF USE AS PESTICIDES

[75] Inventors: Malcolm H. Black; Robert J. Blade; Robert J. Peek, all of Berkhamsted, England

[73] Assignee: Burroughs Wellcome Co., Research Triangle Park, N.C.

[21] Appl. No.: 940,561

[22] Filed: Dec. 11, 1986

[30] Foreign Application Priority Data

Dec. 17, 1985 [GB] United Kingdom ............. 8531072

[51] Int. Cl.$^5$ ..................... A61K 31/66; C07F 9/24
[52] U.S. Cl. ................................ 514/120; 558/151; 558/178
[58] Field of Search .............. 558/171, 178; 564/204; 514/120

[56] References Cited

U.S. PATENT DOCUMENTS 3,833,623 9/1974 Magee ..................... 558/88
3,885,032 5/1975 Magee ..................... 514/120
3,914,417 10/1975 Magee .................... 514/120

FOREIGN PATENT DOCUMENTS 0111105 6/1984 European Pat. Off.
0164187 12/1985 European Pat. Off.
0143593 12/1986 European Pat. Off.
228853 7/1987 European Pat. Off.

OTHER PUBLICATIONS

Derwent Abstract for Su 300471 (6/23/71).

*Primary Examiner*—Mary C. Lee
*Assistant Examiner*—Michael G. Ambrose
*Attorney, Agent, or Firm*—Nixon & Vanderhye

[57] ABSTRACT

A compound of Formula (I):

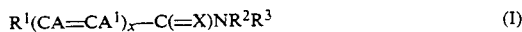

$$R^1(CA=CA^1)_x-C(=X)NR^2R^3 \quad (I)$$

where $R^1$ is alkyl optionally substituted by a group selected from alkoxy, alkenyl, alkynyl, alkenyloxy, alkynyloxy, aryl, aryloxy, arylalkoxy and cycloalkyl fused to an aryl ring; $x=1$ or 2; $X=O$ or $S$; each $A$ and $A^1$ is independently hydrogen, alkyl or haloalkyl; $R^2$ is alkyl, alkenyl or cycloalkyl any of which may be substituted by halo, alkenyl, alkyl, cycloalkyl, alkynyl, dioxalanylalkyl or alkoxy; and $R^3$ is selected from groups (A) to (D):

(A) $-Y=X^1-(R^4)_a$ where $X^1$ is O or S, Y is phosphorus or carbon, $R^4$ is hydrogen, alkyl, alkoxy, acyl or $CO_2R^5$ is alkyl or aryl, and a is 1 or 2.

(B) $-S(R^6)(O)_b$ where $R^6$ alkyl, aryl, aryloxy, alkoxy, thioalkoxy, thioaryl, alkythio, alkoxythio or arylthio and b is 0, 1 or 2

(C) $-S(O)_cNR^7R^8$ where c is 0, 1 or 2, $R^7$ is $-COR^9$ or $-CO_2R^9$ where $R^9$ is hydrogen, alkyl or a fluorine atom, a group (A) or (B) as defined above, or alkyl substituted by acyl, carboalkoxy or cyano, and $R^8$ is alkyl (D) $R^1-(CA=CA^1)_n-C(=X)N(R^2)-$ wherein the substituents are independently selected as in Formula (I) above.

7 Claims, No Drawings

N-ALKYL-N-[1,3-BUTADIENYL(THIO)CARBONYL]-(THIO) PHOSPHORAMIDATES, COMPOSITIONS, AND METHODS OF USE AS PESTICIDES

This invention relates to pesticidal compounds.

Several recent publications have disclosed certain lipid amides as being insecticides and acaricides, for example EP-A-111 105, and EP-A-164 187 (The Wellcome Foundation Limited). Such compounds are secondary or tertiary amides in which the N substituents are generally hydrogen and an alkyl group or two alkyl groups. It has now been found that certain other tertiary amides generally having a heteroatom attached to the amide nitrogen have pesticidal activity.

U.S. Pat. No. 3,896,193 (Chevron) discloses certain phosphorothioates as reactants in the production of insecticides, but does not disclose any having an unsaturated bond conjugated to the carbonyl group, and does not ascribe insecticidal activity to the compounds.

Accordingly, one aspect of the invention provides compounds of Formula (I)

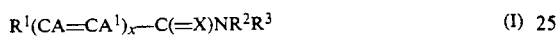

where $R^1$ is alkyl optionally substituted by a group selected from alkoxy, alkenyl, alkynyl, alkenyloxy, alkynyloxy, aryl, aryloxy, arylalkoxy and cycloalkyl fused to an aryl ring;
$x = 1$ or 2;
$X = O$ or $S$;
each A and $A^1$ is independently hydrogen, alkyl or haloalkyl;
$R^2$ is alkyl, alkenyl or cycloalkyl any of which may be substituted by halo, alkenyl, alkyl, cycloalkyl, alkynyl, dioxalanylalkyl or alkoxy; and
$R^3$ is selected from groups (A) to (D):
  (A) $-Y=X^1-(R^4)_a$ where $X^1$ is O or S, Y is phosphorus or carbon, $R^4$ is hydrogen, alkyl, alkoxy, acyl or $CO_2R^5$ where $R^5$ is alkyl or aryl, and a is 1 or 2
  (B) $-S(R^6)(O)_b$
  where $R^6$ is alkyl, aryl, aryloxy, alkoxy, thioalkoxy, thioaryl, alkythio, alkoxythio or arylthio and b is 0, 1 or 2
  (C) $-S(O)_cNR^7R^8$
  where c is 0, 1 or 2, $R^7$ is $-COR^9$ or $-CO_2R^9$ where $R^9$ is hydrogen, alkyl or a fluorine atom, a group (A) or (B) as defined above, or alkyl substituted by acyl, carboalkoxy or cyano, and $R^8$ is alkyl
  (D) $R^1-(CA=CA^1)_n-C(=X)N(R^2)-$
wherein the substituents are independently selected as in Formula (I) above.

Preferably $R^1$ in Formula (I) is alkyl or a group (M) or (N):
  (M) is $Ar(CH_2)_m$
  (N) is $Ar(CH_2)_nO(CH_2)_pQ(CH_2)_q$
wherein Ar is phenyl, furyl, thienyl, benzofuranyl, benzopyranyl, chromanyl, indanyl, tetrahydronaphthyl or naphthyl, any of which may be substituted by one or more of halogen, alkyl, halo-alkyl (e.g. trifluoromethyl) alkoxy, halo-alkoxy, halo and alkenyl,
  $m = 1$ to 8,
  $n = 0$ or 1,
  $p = 0$ to 6,
  $q = 0$ to 6, and
  Q is $-O-$ or $-CH_2-$.

Preferably in Formula (I), A and $A^1$ are both hydrogen and/or $x = 2$ and/or X is oxygen and/or $R^2$ is alkyl, most preferably isobutyl, 1,2-dimethylpropyl, 2,2-dimethylpropyl or 2-methyl-2-propenyl. 1,2-Dimethylpropyl has been found to be associated with acaricidal activity.

Another aspect of the invention provides a process for preparing a compound of Formula (I)
  (a) when X is oxygen, by reaction of a compound of Formula (II) with a compound of Formula (III)

where B is a leaving group such as chlorine and M is H or preferably a metal e.g. lithium, or
  (b) by reaction of a compound of Formula (IV) with a compound of Formula (V):

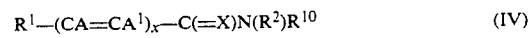

where $R^{10}$ is hydrogen or preferably trialkylsilyl and $X^2$ is a leaving group, preferably chlorine.

Process (a) is carried out in an aprotic solvent such as tetrahydrofuran in the absence of moisture at low temperature. Compounds of Formula (II) where B is chlorine can be prepared from the corresponding carboxylic acid by reaction with a suitable reagent such as oxalyl chloride or thionyl chloride.

The aforementioned carboxylic acid may be prepared by any of the routes detailed in European Patent documents 111 105 and 164 187.

Compounds of Formula (III) may be prepared by reaction of the parent amine $HN(R^2)R^3$ with a base such as n-butyllithium in an anhydrous aprotic solvent such as tetrahydrofuran.

Compounds of Formula (V) where $R^3$ is the group (C) are obtained by reaction of a compound $HN(R^8)R^7$ with sulphur dichloride in an aprotic solvent, e.g. dichloromethane in the presence of a base, e.g. triethylamine.

Process (b) is carried out in an aprotic solvent such as tetrahydrofuran in the absence of moisture. If $R^{10}$ is trialkylsilyl, then such compounds can be prepared from the corresponding secondary amides by reaction with a silylating agent such as bis-trimethylsilyl acetamide in an aprotic solvent such as acetonitrile or pyridine in the absence of moisture.

The aforementioned secondary amides may be prepared by any of the routes detailed in the patent applications noted above.

The compounds of Formula I may be used to control arthropods such as insects and acarines.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapour emanator (e.g. coil, mat or the like), granule, aerosol, oil suspensions, oil solutions, pressure-pack, impregnated article (such as a plastics ear tag or collar or a strip to treat the air of an enclosed space) or pour on formulation. Dip concentrates are not applied per se, but diluted with water and the animals immersed in a dipping bath containing the dip wash. Sprays may be applied by hand or by means of a spray race or arch. The animal, plant or surface may be saturated with the spray by means of high volume application or superficially coated with the spray by means of light or ultra low volume application. Aqueous suspensions may be applied to the animal in the same manner as sprays or dips. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil), a wettable powder or a controlled release formulation, such as a microencapsulated formulation. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use. Microencapsulated formulations may be made by any known technique, for example coacervation or inter-facial polymerisation.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. Aqueous solutions may also be formed from acid addition salts of a compound of the Formula (I). The suspensions or solutions may be applied per se or in a diluted form in known fashion. Electrostatic spraying techniques may be used with suitable formulations.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting then with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium which also contains a viscous oil to minimise spreading of the formulation on the surface of the animals. An avian or mammal host may also be protected against infestation of acarine ectoparasites by means of carrying a suitably-moulded, shaped plastics articles impregnated with a compound of Formula (I). Such articles include impregnated collars, tags, bands, sheets and strips suitably attached to appropriate parts of the body.

The concentration of the compound of Formula (I) to be applied to a locus (e.g. animal, grain, crop, soil, building etc.) will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%. For public health usage, a deposited concentration of up to about 5% may be needed. The concentrate may contain up to 90% active ingredient.

Dusts, greases, pastes and aerosol formulations are usually applied in a random fashion as described above and concentrations of 0.001 to 20% w/v of a compound of Formula (I) in the applied formulation may be used.

Bait formulations for, for example, cockroaches will include suitable attractants and/or foodstuffs. The compounds of the invention can be formulated specifically for use on grain or on the exposed surfaces of buildings, or for space spraying.

The compounds may be administered in an animal's feed to combat insect larvae infesting the animal's dung. Any suitable formulation, including microencapsulated material, may be used. The amount of the compound which is administered will vary according to the type and size of animal, and is chosen to provide a suitable concentration of the compounds in the animal's dung. Typically, 0.001 to 100 mg/kg bodyweight, preferably 0.1 to 10 mg/kg, are administered daily, to give concentrations of 0.001 to 1%, preferably 0.01 to 0.1% compound in the dung. The compound will usually be formulated as a concentrate or premix for mixing with a feed supplement, feed concentrate, roughage or the like. Alternatively, the compound may be added to the supply of drinking water. Suitable animals include cattle, pigs, horses, sheep, goats and poultry.

Insect pests include members of the orders Coleoptera (e.g. Anobium, Tribolium, Sitophilus, Diabrotica, Anthonomus, Hylotrupes or Anthrenus spp.), Lepidoptera (e.g. Ephestia, Plutella, Chilo, Heliothis, Spodoptera, Tinea or Tineola spp.), Diptera (e.g. Anopheles, Simulium, Musca, Aedes, Culex, Glossina, Stomoxys, Haematobia, Tabanus, Hydrotaea, Lucilia, Chrysomia, Callitroga, Dermatobia, Hypoderma, Liriomyza, and Melophagus spp.), Phthiraptera (Malophaga e.g. Damalina spp. and Anoplura e.g. Linognathus and Haematopinus spp.), Hemiptera (e.g. Triatoma, Rhodnius, Aphis, Bemisia, Aleurodes, Nilopavata, Nephrotetix or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.)] Siphonaptera (e.g. Ctenocephalides or Pulex spp.), Thysanura (e.g. Lepisma spp.), Dermaptera (e.g. Forficula spp.) and Psocoptera (e.g. Peripsocus spp.). Acarine pests include ticks, e.g. members of the genera Boophilus, Rhipicephalus, Amblyomma, Hyaloma, Ixodes, Haemaphysalis, Dermocentor and Anocentor, and mites and manges such as Tetranychus, Psoroptes, Psorergates, Chorioptes, Demodex, Dermatophagoides, Acarus, Tyrophagus and Glycyphagus Spp.

The compounds exhibit killing and/or knockdown activity against adult and/or larval arthropod pests.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:
(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of insect or acarine pests comprising the application to the pest or its environment of a compound of Formula (I);
(f) synergised pesticidal compositions comprising a compound of Formula (I); and
(g) potentiating or non-potentiating mixtures of a compound of Formula (I) and another pesticidal compound;
(h) novel intermediates in the preparation of compounds of Formula (I), particularly compounds of Formula (II).

The following Examples illustrate, in a non-limiting manner, preferred aspects of the invention. All temperatures are in degrees Celsius.

EXAMPLE 1

(2E,4E)-N-Isobutyl-N-phenylsulphenyl 8-phenylocta-2,4-dienamide

Diphenyl disulphide (9.81 g) was added to a solution of silver nitrate (7.8 g) in methanol (400 ml). Isobutylamine (22.3 ml) was added with cooling and the mixture stirred at room temperature for 24 hrs. After filtration the filtrate was concentrated and the crude sulphenamide purified by short path distillation.

The above sulphenamide (1 g) in anhydrous tetrahydrofuran (30 ml) was treated at $-60°$ C. with n-butyl lithium in hexane (4.2 ml, 1.6 Mol). After 3 hrs at $-60°$ C., (2E,4E) 8-phenylocta-2,4-dienyl chloride (6.7 mmol) (prepared from (2E,4E) 8-phenylocta-2,4-dienoic acid (1.45 g), oxalyl chloride (589 microlitres), dimethyl formamide (4 drops) in dichloromethane (15 ml)) was added at $-70°$ C. After 2 hrs at $-50°$ to $-60°$ C., reaction was worked up and the crude product purified by flash column chromatography (silica-ether/hexane) to give partially purified material. The latter was purified by chromatography further (Silica; 5→12% ether in hexane) to give (2E,4E)-N-isobutyl-N-phenylsulphenyl 8-phenylocta-2,4-dienamide as a pale yellow oil. Tlc.; Silica, 20% ether in hexane, 1 spot, Rf 0.37. 1R; $\nu$max (neat) 1670, 1638, 1611. NMR (CDCl$_3$); 7.2 (11H), m,SPh, Ph, H3; 6.77 (1H), d, H2; 6.01 (2H), m, H4,5; 3.47 (2H),d,Bu$^i$; 2.54 (2H), t,H8; 2.20(2H),m,H6; 1.9(3H),m,H7,Bu$^i$, 0.94 (6H),Bu$^i$.

EXAMPLE 2

(2E,4E)-Diethyl N-hexa-2,4-dienoyl-N-isobutylamido phosphate.

Diethyl N-isobutyl phosphoramidate (1 g), prepared by literature method, from diethylchlorophosphate and isobutylamine, in anhydrous tetrahydrofuran (30 ml), was treated at $-60°$ (with n-butyl lithium in hexane (3 ml at 1.6M). After 3 hours at $-60°$ C., (2E,4E) hexa-2,4-dienoyl chloride (506 μl.) was added. After a subsequent 3 hours at $-50°$ to $-60°$ the reaction mixture was worked-up in standard fashion and the crude material purified by column chromatography (Silica; 1:1 ether-hexane ether) to give (2E,4E)-diethyl N-hexa-2,4-dienoyl-N-isobutylamido phosphate as a pale yellow oil Tlc.; Silica-ether 1 spot, R$_f$0.47; NMR; 7.2 (1H),m, H3; 6.43(1H),d,H2; 6.80 (2H),m,H4,5; 4.15 (4H),m,(OEt)$_2$; 3.55(2H) d of d, Bu$^i$; 1.9(1H),m,Bu$^i$; 1.87 (3H),d,H6; 1.36 (6H),t,(OEt)$_2$; 0.94 (6H),d,dBu$^i$.

EXAMPLE 3

(2E,4E) Methyl N-isobutyl-N-[9-(3'-trifluoromethyl-benzyloxy)nona-2,4-dienoyl]oxamate (2E,4E) N-Isobutyl 9-(3'-trifluoromethylbenzylozy)-nona-2,4-dienamide (0.5 g) (prepared according to the previous patent applications) in dry acetonitrile (6 ml) was treated with (bis-trimethylsilyl) acetamide (387 μl.). After 18 hours at room temperature, warming to 80° and cooling to room temperature again, the volatile materials were removed in vacuo with warming to 50°. After cooling, the residue was dissolved in tetrahydrofuran and treated with methyl oxalyl chloride (190 μl.) under nitrogen. After several hours at room temperature the reaction was worked-up in standard fashion.

The crude material was purified by column chromatography (Silica; 5–30% ether in hexane) to give the product as a straw coloured oil. Tlc; Silica-ether, $R_f$ 0.70, 1 spot; NMR; 7.37 (4H),m,aryl,H3; 6.15 (2H),d,H2; 6.18 (2H), H4,5; 4.50(2H), S, benzyl $CH_2$; 3.81 (3H), S, Me; 3.78 (2H),d,$Bu^i$; 3.49 (2H),t,H9; 2.19(2H),m,H6; 2.7(5H),m,H6,7,$Bu^i$; 0.93 (6H),d,$Bu^i$.

By analogous methods the compounds of the following examples were made:

TABLE 1

$R^1(CH=CH)_2—CONR^2R^3$

| Example No. | $R^1$ | $R^2$ | $R^3$ |
|---|---|---|---|
| 4 | $CH_3(CH_2)_4$ | isobutyl | $CO.(CH_2)_4CH_3$ |
| 5 | Me | isobutyl | SPh |
| 6 | $CH_3(CH_2)_4$ | isobutyl | SPh |
| 7 | $Ph(CH_2)_3$ | 1,2-dimethyl-propyl | SPh |
| 8 | $Ph(CH_2)_3$ | isobutyl | $(OEt)_2P=O$ |
| 9 | $CH_3(CH_2)_4$ | isobutyl | $CO.CO_2Me$ |
| 17 | $CH_3(CH_2)_4$ | isobutyl | $(OEt)_2P=O$ |
| 18 | $CH_3(CH_2)_4$ | isobutyl | $CO.CO_2Et$ |
| 19 | 3,5-dichloro-$—C_6H_3—O(CH_2)_7$ | isobutyl | $(OEt)_2P=O$ |

TABLE 2

$ArCH_2O(CH_2)_4(CH=CH)_2CONR^2R^3$

| | Ar | $R^2$ | $R^3$ |
|---|---|---|---|
| 10 | 3-Trifluoromethyl phenyl | isobutyl | —SPh |
| 11 | 3-Trifluoromethyl phenyl | isobutyl | $—CO.CO_2Ph$ |
| 12 | 3-Trifluoromethyl phenyl | isobutyl | —SNMe.CHO |
| 13 | 3-Trifluoromethyl phenyl | isobutyl | $S—NMe.CO_2Me$ |
| 14 | 3-chlorophenyl | isobutyl | —SPh |
| 15 | 3-chlorophenyl | 1,2-dimethyl propyl | —SPh |
| 16 | 3-chlorophenyl | isobutyl | —S-(4-Me-phenyl) |

EXAMPLE 20

(2E) Diethyl N-(but-2-enoyl)-N-isobutylamidophosphate

| Example No. | $R_f$ | Solvent |
|---|---|---|
| 1 | 0.37 | 1:4 ether/hexane |
| 2 | 0.47 | ether |
| 3 | 0.70 | ether |
| 4 | 0.73 | ether |
| 5 | 0.52 | 1:1 ether/hexane |
| 6 | 0.42 | 3:7 ether/hexane |
| 7 | 0.66 | ether |
| 8 | 0.48 | ether |
| 9 | 0.59 | ether |
| 10 | 0.70 | ether |
| 11 | 0.33 | 1:1 ether/hexane |
| 12 | 0.25 | 1:1 ether/hexane |
| 13 | 0.73 | ether |
| 14 | 0.23 | 1:4 ether/hexane |
| 15 | 0.47 | ether |
| 16 | 0.14 | 1:9 ether/hexane |
| 17 | 0.51 | ether |
| 18 | 0.70 | ether |
| 19 | 0.50 | ether |
| 20 | 0.31 | ether |

Biological activity

A. Topical application on houseflies

Compounds of the invention were administered topically in cellosolve solution in conjunction with 6 μg piperonyl butoxide to adult female *Musca domestica* (WRL strain) and the dose for 50% mortality ($LD_{50}$) was determined. The results are given in Table A:

TABLE A

| Compound | $LD_{50}$ (μg/fly) |
|---|---|
| 1 | <6 |
| 2 | c 0.3 |
| 3 | <3 |
| 7 | >6 |
| 10 | c 1.5 |
| 11 | c 0.6 |
| 14 | c 1.5 |
| 15 | <3 |
| 16 | <3 |
| 17 | <3 |
| 18 | <3 |
| 19 | <3 |
| 20 | >0.6, <3 |

B. Topical activity on cockroaches

The compounds were administered topically in cellosolve solution in conjunction with piperonyl butoxide to adult *Blattella germanica*. The results are given in Table B.

TABLE B

| Compound | $LD_{50}$ (μg/insect) |
|---|---|
| 2 | <2 |
| 15 | <10 |

C. Acaricidal activity

In injection into adult female *Boophilus microplus*, the compound of Example 7 gave 90% inhibition of reproduction at 10 micrograms per tick.

FORMULATIONS

| 1. Emulsifiable Concentrate | |
|---|---|
| Compound of Example 1 | 10.00 |
| Ethylan KEO | 20.00 |
| Xylene | 67.50 |
| Butylated Hydroxyanisole | 2.50 |
| | 100.00 |
| 2. Wettable Powder | |
| Compound of Example 1 | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |

-continued

| | |
|---|---|
| | 100.00 |
| 3. Dust | |
| Compound of Example 1 | 0.50 |
| Butylated Hydroxyanisole | 0.10 |
| Talc | 99.40 |
| | 100.00 |
| 4. Bait | |
| Compound of Example 1 | 40.25 |
| Icing Sugar | 99.65 |
| Butylated hydroxy toluene | 0.10 |
| | 100.00 |
| 5. Lacquer | |
| Compound of Example 1 | 2.5 |
| Resin | 5.0 |
| Butylated Hydroxy anisole | 0.5 |
| High aromatic white spirit | 92.0 |
| | 100.00 |
| 6. Aerosol | |
| Compound of Example 1 | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound of Example 1 | 0.1 |
| Butylated Hydroxy anisole | 0.1 |
| Xylene | 10.0 |
| Odourless Kerosene | 89.8 |
| | 100.00 |
| 8. Potentiated Spray | |
| Compound of Example 1 | 0.1 |
| Permethrin | 0.1 |
| Butylated Hydroxyanisole | 0.1 |
| Xylene | 10.1 |
| Odourless Kerosene | 89.8 |
| | 100.0 |

We claim:

1. A compound of Formula (I):

$$R^1(CA=CA^1)_2-C(=X)NR^2R^3 \quad (I)$$

where $R^1$ is $C_{1-13}$ alkyl unsubstituted or substituted by a group selected from phenyl, phenoxy, phenyl(lower)alkoxy optionally substituted by one or more of lower alkyl, halo(lower)alkyl, lower alkoxy, halo(lower)alkoxy, halo and lower alkenyl thereof; X=O or S; each A and $A^1$ is independently hydrogen, lower alkyl or halo(lower)alkyl; $R^2$ is lower alkyl; and $R^3$ is $-Y=X^1-(R^4)_2$ where $X^1$ is O or S, Y is phosphorus, and $R^4$ is lower alkoxy.

2. A compound of Formula (I):

$$R^1(CA=CA^1)_2-C(=X)NR^2R^3 \quad (I)$$

wherein $R^1$ is unsubstituted $C_{1-13}$ alkyl or a group (M) or (N) as defined below:

(M) is Ar $(CH_2)_m$ (N) is Ar $(CH_2)_nO(CH_2)_pQ(CH_2)_q$ wherein Ar is unsubstituted phenyl or phenyl substituted by one or more of halogen, lower alkyl, halo(lower)alkyl, lower alkoxy, halo(lower)alkoxy, halo and lower alkenyl, m=1 to 8, n=0 or 1, p=0 to 6, q=0 to 6, and Q is $-O-$ or $-CH_2-$; X=O or S; each A and $A^1$ is independently hydrogen, lower alkyl or halo(lower)alkyl; $R^2$ is lower alkyl; and $R^3$ is $-Y=X^1-(R^4)_2$ where $X^1$ is O or S, Y is phosphorus, and $R^4$ is lower alkoxy.

3. A compound according to claim 1 or 2 wherein A and $A^1$ are both hydrogen.

4. A compound according to claim 1 or 2 wherein X is oxygen.

5. A compound according to claim 1 or 2 wherein $R^2$ is isobutyl, 1,2-dimethylpropyl, 2,2-dimethylpropyl or 2-methyl-2-propenyl.

6. A pesticidal composition comprising a pesticidally effective amount of a compound according to claim 1 or 2 and a carrier.

7. A method of combatting pests by applying to the pest or its locus a compound according to claim 1 or 2.

* * * * *